United States Patent
O'Sullivan

(10) Patent No.: US 12,370,231 B2
(45) Date of Patent: Jul. 29, 2025

(54) COMPOSITIONS FOR INHIBITING DEGRADATION OF HYALURONIC ACID AND METHODS OF USE THEREOF

(71) Applicant: Epidarus Therapeutics, LLC, Doylestown, PA (US)

(72) Inventor: Deirdre O'Sullivan, Doylestown, PA (US)

(73) Assignee: Epidarus Therapeutics, LLC, Doylestown, PA (US)

( * ) Notice: Subject to any disclaimer, the term of this patent is extended or adjusted under 35 U.S.C. 154(b) by 162 days.

(21) Appl. No.: 17/905,926

(22) PCT Filed: Mar. 3, 2021

(86) PCT No.: PCT/US2021/020688
§ 371 (c)(1),
(2) Date: Sep. 8, 2022

(87) PCT Pub. No.: WO2021/188295
PCT Pub. Date: Sep. 23, 2021

(65) Prior Publication Data
US 2023/0165923 A1  Jun. 1, 2023

Related U.S. Application Data

(60) Provisional application No. 62/990,676, filed on Mar. 17, 2020.

(51) Int. Cl.
| | |
|---|---|
| *A61K 36/536* | (2006.01) |
| *A61K 8/9783* | (2017.01) |
| *A61K 8/9789* | (2017.01) |
| *A61K 36/18* | (2006.01) |
| *A61K 36/185* | (2006.01) |
| *A61Q 19/00* | (2006.01) |

(52) U.S. Cl.
CPC .......... *A61K 36/536* (2013.01); *A61K 8/9783* (2017.08); *A61K 8/9789* (2017.08); *A61K 36/18* (2013.01); *A61K 36/185* (2013.01); *A61Q 19/007* (2013.01)

(58) Field of Classification Search
CPC .. A61K 36/536; A61K 8/9783; A61K 8/9789; A61K 36/18; A61K 36/185; A61K 2236/00; A61K 36/57; A61K 2800/782; A61K 8/9728; A61Q 19/007; A61Q 17/04; A61Q 19/00; A61Q 19/08; A23K 10/30; A61P 13/08; A61P 13/10; A61P 17/00; A61P 17/08; A61P 19/02; A61P 29/00; A23L 33/105
See application file for complete search history.

(56) References Cited

U.S. PATENT DOCUMENTS

| | | |
|---|---|---|
| 5,882,664 A | 3/1999 | Soma et al. |
| 2006/0165816 A1 | 7/2006 | Tze et al. |
| 2012/0148636 A1 | 6/2012 | Berrido et al. |
| 2013/0171278 A1 | 7/2013 | Lee et al. |
| 2014/0037761 A1 | 2/2014 | Yoon et al. |
| 2016/0206540 A1* | 7/2016 | Hood .................. A61K 8/4973 |
| 2018/0344661 A1* | 12/2018 | Finley .................. A61P 35/00 |

FOREIGN PATENT DOCUMENTS

| | | |
|---|---|---|
| CN | 101036771 A | 9/2007 |
| CN | 101371700 A | 2/2009 |
| KR | 2013-0086682 A | 8/2013 |
| WO | WO 03/084522 A1 | 10/2003 |
| WO | WO 2014/083438 A2 | 6/2014 |

OTHER PUBLICATIONS

International Search Report for PCT/US2021/020688 dated May 6, 2021.
Supplementary Partial European Search Report for EP 21771238.

* cited by examiner

*Primary Examiner* — Aaron J Kosar
*Assistant Examiner* — Jennifer Lynn Cain
(74) *Attorney, Agent, or Firm* — Knobbe Martens Olson & Bear LLP

(57) ABSTRACT

The present disclosure relates to compositions containing natural plant extracts that inhibit Hyaluronidase 1 and their use in effectively treating conditions such as dryness of skin and lips, skin damage due to UV radiation, chronic inflammatory conditions affecting the skin, the urinary bladder or prostate, osteoarthritis and joint pain, and also promoting wound healing.

14 Claims, 8 Drawing Sheets

COMPOSITIONS FOR INHIBITING DEGRADATION OF HYALURONIC ACID AND METHODS OF USE THEREOF

CROSS REFERENCE TO RELATED APPLICATIONS

This application is a U.S. National Phase Application of PCT International Application Number PCT/US2021/020688, filed on Mar. 3, 2021, designating the United States of America and published in the English language, which is an International Application of and claims the benefit of priority to U.S. Provisional Application No. 62/990,676, filed on Mar. 17, 2020. The disclosures of the above-referenced applications are hereby expressly incorporated by reference in their entireties.

FIELD OF THE INVENTION

Aspects of the present disclosure relate to compositions comprising a plant extract such as an extract of Prunella, Star Anise, Linden or any combination thereof, which can be used to inhibit enzymatic degradation of hyaluronic acid (HA), especially in methods of treating, inhibiting, or ameliorating HA-mediated inflammation, diseases or other conditions, improving wound healing or wound closure, reducing histamine or tryptase release, inhibiting hyaluronic acid degradation, or increasing hyaluronic acid presence in chondrocytes or synoviocytes in a subject, such as a human or animal.

BACKGROUND OF THE INVENTION

Hyaluronic Acid (HA) is a ubiquitous material found naturally as part of the extracellular matrix in most body tissues including, brain, cartilage, blood vessels, skin, and umbilical cord. High concentrations of soluble HA are also found in synovial joint fluid and in the vitreous humor of the eye. One of the most important biological functions of HA is water retention. HA also advantageously provides nutrients to and removes waste from cells that do not have a direct blood supply, such as cartilage and epidermal cells. The ability of HA to bind water gives structure to tissues, lubricates and cushions moveable parts of the body, such as joints (e.g., knee) and muscles, and contributes to the skin's volume and elasticity. In other tissues, such as the bladder, glycosaminoglycans, including HA, form a protective layer over the bladder epithelium, shielding it from damage and irritation caused by urine constituents.

However, these beneficial properties are highly dependent on chain length. HA is a large polymer composed of alternating residues of $\beta$-D-(1→3) glucuronic acid and $\beta$-D-(1→4)-N-acetylglucosamine. Some HA molecules can have a molecular mass of over $10^7$ Da in—e.g., often referred to as High Molecular Weight HA (HMW-HA). HA may also exist in multiple smaller forms, referred to as Low Molecular Weight HA (LMW-HA).

Metabolism of HA in the body is regulated by an interplay between synthetic enzymes (HA synthases) and degradative enzymes (hyaluronidases, also called hyaluronoglucosaminidases), principally HYAL1 and HYAL2. It is thought that HYAL2 degrades HA into intermediate-length fragments of about 20 kDa and HYAL1 degradation yields tetra-saccharides of molecular mass of approximately 777 Da. Hyaluronidases hydrolyze the hexosaminidic $\beta(1-4)$ linkages between N-acetyl-d-glucosamine and d-glucuronic acid residues in HA, thereby releasing HA fragments. Additionally, reactive oxygen species accumulate at sites of tissue injury and may also provide a mechanism for generating HA fragments. HA has an extremely high turnover rate under normal physiological conditions and its degradation is markedly accelerated following tissue injury or damage.

The functions of HA extend beyond its roles as a structural component of the extracellular matrix and as a tissue and joint lubricant. HA also serves as a sophisticated information system, and the messages it transmits depend on its molecular size. HA exists in both pro- and anti-inflammatory forms, with HMW-HA being immunosuppressive and, by contrast, LMW-HA fragments, particularly the HA tetrasaccharides generated by HYAL1 degradation, being highly angiogenic, immunostimulatory and inflammatory. In general, small HA fragments act as Damage Associated Molecular Patterns (DAMPS), which communicate with monitoring cells of the immune system to indicate that tissue injury has occurred. These sentinel cells of the innate immune system, such as mast cells, macrophages and dendritic cells, then activate a full-blown immune response. Often, the immune response is appropriate and resolves once the threat has passed, but chronic low-level inflammation can persist and contribute to diseases such as osteoarthritis, bladder interstitial cystitis, benign prostatic hyperplasia (BPH), chronic prostatitis (aka chronic pelvic pain syndrome) and rosacea. Inappropriate generation of HA fragments can drive chronic long-term immune activation and contribute to the pathology of these conditions.

Osteoarthritis (also referred to as wear-and-tear arthritis) is the most common joint disease, affecting up to 27 million adults in the United States alone. It is the leading cause of chronic disability in people over 70 years of age. While not life-threatening, osteoarthritis is painful, progressive and has a large negative impact on the quality of life for affected individuals. Further, the incidence of osteoarthritis is growing as the U.S. population ages. There are several risk factors for osteoarthritis, including aging, obesity, injury, genetic pre-disposition, and dietary/metabolic deficiencies. Osteoarthritis is a multi-factorial, degenerative disease. In affected joints, cartilage, subchondral bone and the synovium show damage and destruction.

The degradation of HA plays a significant role in osteoarthritis and its progression. In joints, HA is degraded by hyaluronidases, with HYAL1 reportedly playing a major role. Cartilage is predominantly made up of a number of specialized proteins which link to HA to form a compressible, shock-absorbing cushion between bones. Breakdown of HA results, ultimately, in bone rubbing on bone during movement, which is very painful. Also, the lubricating or gliding properties of synovial fluid, which bathes joints, is significantly dependent on the water-binding ability of intact HA molecules. This lubrication is lost when the HA is degraded by hyaluronidases or by reactive oxygen species, further adding to the stress on affected joints.

There is currently no effective treatment for osteoarthritis. Rather, the first line of treatment involves the use of non-steroidal anti-inflammatory drugs (NSAIDs) such as Aspirin, Ibuprofen or Naproxen. While these drugs may treat the pain associated with osteoarthritis and are anti-inflammatory, they do not halt the progression of the disease and also cause side effects that limit their long-term use. Prescription NSAIDs, such as Celebrex®, Sulindac or Diclofenac, are more effective at treating pain but again, do not halt osteoarthritis progression. Joint supplements, such as chondroitin sulfate or glucosamine may also be used. Although chondroitin sulfate is an important molecule in joints and glucosamine is a molecular constituent of HA, there is little solid evidence showing actual efficacy of these supplements in treating osteoarthritis. Another treatment approach involves visco-supplementation with HA, which is a procedure where intact, high molecular weight HA is directly injected into the affected area (usually knee or shoulder). This can restore mobility and relieve pain by providing lubrication and cushioning the joint against painful bone-on-bone abrasion. The injected HA can also reduce inflammation and allow the cartilage to recover some of its protective ability. However, the benefits of HA injection last only a few months, the procedure is painful and, ultimately joint destruction will recur. Yet another treatment involves joint replacement surgery, which is the ultimate answer to the cartilage damage caused by osteoarthritis. Knee replacement surgery has become the most frequently performed surgery in the United States. However, it is major surgery, requiring a hospital stay and average costs can be extremely expensive.

Chronic inflammation is also a pervasive feature of aging, particularly with respect to aging skin. With age, skin loses its ability to balance synthesis and degradation of HA, resulting in a loss of hydration and thinning of the epidermis. The skin becomes fragile, wrinkled and slower to heal from injury. Current cosmeceutical approaches for restoring HA in aging skin include topical application of a wide range of creams and lotions containing HA and direct injection of HMW-HA into the dermis to smooth wrinkles. While effective for many patients, HA injections are painful, expensive and require frequent administration. Also, as HA is an extremely large molecule, its bio-availability from topical applications is low.

Another approach to remediating aging skin involves rejuvenating procedures, such as laser resurfacing, dermabrasion and chemical peels. These popular cosmetic procedures stimulate collagen production in the dermis to rejuvenate the skin. However, the epidermis is severely damaged and patients must wait for a week or more for epidermal healing to occur. The recovery time for these procedures is a major drawback for patients and lessening this time by enhancing the rate of skin re-epithelialization would be a very desirable outcome. HA synthesis and enzymatic processing is central to the necessary epithelial cell replication and migration required for wound healing in the epidermis. Fine tuning the balance between HA synthesis and degradation can speed epidermal healing and increase patient satisfaction following skin rejuvenation treatments.

Tissue inflammation is often characterized by significant infiltration of activated mast cells. Upon activation, mast cells undergo degranulation, and release histamine and other inflammatory molecules that can cause irritation and inflammation. For example, insect bites induce dermal mast cell degranulation, which then releases histamine among other pro-inflammatory molecules. Chronic inflammatory skin conditions, such as dermatitis and rosacea are also associated with increased numbers of activated Mast Cells.

Other chronic conditions, such as Bladder Interstitial Cystitis (BIC) involve Mast Cell infiltration and activation. HA degradation is a hallmark of this condition too and animal models of BIC can be generated by instillation of HYAL1 into the bladder. Conversely, direct instillation of HMW-HA into the bladders of human patients suffering from BIC is reported to reduce inflammation, allow repair of the protective GAG layer and provide temporary symptom relief. BIC is an extremely debilitating and painful condition. Once considered a very rare condition, improved diagnostics now reveal that, in the USA alone, an estimated 3.2 to 7.9 million women (2.7 to 6.5% of women) and 1 to 4 million men suffer from BIC. Similarly, in men, lab models of chronic pelvic pain syndrome have shown that intact HA can diminish the inflammatory signaling that leads to chronic prostate inflammation and to hyperplasia. Liu, M-C. et al. PloS ONE, 2017. There remains a need for new approaches to treat or inhibit HA-mediated conditions such as osteoarthritis, skin aging and appearance (e.g. poor hydration and elasticity), wound healing, rosacea, inflammation from insect bites, interstitial cystitis, BPH, chronic prostatitis and other inflammatory conditions.

SUMMARY OF THE INVENTION

Provided herein are compositions comprising *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladiumfor* or any combination thereof, which inhibit the degradation of hyaluronic acid (HA), such as mediated by HYAL1, and which have a systemic effect in reducing the generation of pro-inflammatory HA fragments (e.g., DAMPS) and/or the loss of HMW-HA and methods of using these compositions to treat, inhibit or ameliorate HA-mediated conditions or diseases, improve wound healing or wound closure, reduce histamine or tryptase release, inhibit HA degradation, or increase HA presence in chondrocytes or synoviocytes in a subject, such as a human or non-human animal. The term "subject" as used herein refers to human or non-human animals including, but not limited to domestic animals (e.g., a dogs or cats) or farm animals (e.g., horse, pig, cattle, sheep, or goats). It has been discovered that extracts (e.g., propanediol extracts or extracts made using a liquid C1-C8 alkane solvent, an alcohol, or a mixed solvent containing an alcohol and a C1-C8 alkane or water) from *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladiumfor* or any combination thereof, preferably compositions comprising two or more of such extracts, are useful for the inhibition or amelioration of the degradation of hyaluronic acid e.g., by inhibiting HYAL-1 or reducing the generation of pro-inflammatory HA fragments (e.g., DAMPS) and/or the loss of HMW-HA in a subject such as a human or non-human animal, for instance domestic animals (e.g., a dogs or cats) or farm animals (e.g., horse, pig, cattle, sheep, or goats). The extracts used in these compositions can be made from any part of the plants referenced above e.g., stems, arils, roots, leaves, inflorescences, or seeds or its roots or root ball and such extracts can be formulated with or without a pharmaceutically, nutraceutically or cosmeceutically acceptable carriers, diluents, preservatives, antioxidants, or excipients.

Restoring HMW-HA by injection or instillation or inhibiting enzymatic degradation of HA has been used by others to treat a variety of conditions but such therapies have considerable drawbacks. Some approaches, for example require administration of the drug, pentosan polysulfate. This drug is used to treat osteoarthritis in animals (CARTROPHEN™) and for bladder interstitial cystitis in humans (ELMIRON®). The drug reportedly acts by inhibiting hyaluronidase degradation of HA in joints and bladder epithelium. However, its use is limited because it is a heparin-like molecule that affects blood coagulation and it is known to be poorly bio-available and to cause several undesirable side effects. In the United States, ELMIRON® (pentosan polysulfate sodium) is FDA-approved in capsule form and its use in humans is only permitted for the relief of bladder pain or discomfort associated with interstitial cystitis. It is not FDA-approved for treatment of osteoarthritis in either humans or animals.

The compositions and methods described herein, preferably comprising an extract of Prunella, Star Anise, Linden or any combination thereof with or without an extract of Allspice, unexpectedly provide unique approaches to treat, inhibit, or ameliorate HA-mediated conditions or diseases by inhibiting the degradation of hyaluronic acid (HA), such as is mediated by HYAL1, and/or reducing the generation of pro-inflammatory HA fragments (e.g., DAMPS) and/or the loss of HMW-HA in a subject such as a human or non-human animal, for instance domestic animals (e.g., a dogs or cats) or farm animals (e.g., horse, pig, cattle, sheep, or goats). Accordingly, methods of using these compositions to treat, inhibit or ameliorate HA-mediated conditions or diseases, improve wound healing or wound closure, reduce histamine or tryptase release, inhibit HA degradation, or increase HA presence in chondrocytes or synoviocytes in a subject such as a human or non-human animal, for instance domestic animals (e.g., a dogs or cats) or farm animals (e.g., horse, pig, cattle, sheep, or goats) are embodied herein. The aforementioned compositions can also be used to treat, inhibit, or ameliorate osteoarthritis, rosacea, inflammation, e.g., inflammation or itching from insect bites, bladder interstitial cystitis, BPH, chronic prostatitis or other inflammatory conditions e.g., chronic inflammation associated with joint pain synovitis, or arthritis, as well as, inflammatory bowel disease, Crohn's disease or ulcerative colitis in a subject such as a human or non-human animal, for instance domestic animals (e.g., a dogs or cats) or farm animals (e.g., horse, pig, cattle, sheep, or goats). The compositions and methods described herein also unexpectedly provide unique approaches to improve additional HA-mediated conditions such as reducing, inhibiting, or ameliorating skin aging or improving skin appearance e.g., by improving hydration or elasticity of skin or enhancing or accelerating wound healing in a subject. Acceleration of epithelial wound healing through effects on HA processing achieved by administration of any one or more of the compositions described herein also provide unique approaches to treat or ameliorate epidermal damage incurred during radiation therapy, laser skin re-surfacing, skin peels, dermabrasion or microneedling in a subject. Damage to oral epithelium, caused by periodontitis or by oral surgery, can also be ameliorated in a subject by administration of any one or more of the compositions described herein, preferably comprising an extract of Prunella, Star Anise, Linden or any combination thereof.

By some approaches, a composition comprising, consisting essentially of or consisting of an extract (e.g., a propanediol extract or extracts made using a liquid C1-C8 alkane solvent, an alcohol, or a mixed solvent containing an alcohol and a C1-C8 alkane or water) of *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladiumfor* or any combination thereof, preferably compositions comprising two or more of such aforementioned extracts, is provided or administered to a subject such as a human or non-human animal, for instance domestic animals (e.g., a dogs or cats) or farm animals (e.g., horse, pig, cattle, sheep, or goats) in need thereof e.g., orally, rectally, vaginally, parenterally, or topically so as to treat, inhibit, or ameliorate HA-mediated conditions or diseases including but not limited to skin aging, damage to oral mucosal layers, osteoarthritis, rosacea, inflammation, e.g., inflammation or itching from insect bites, bladder interstitial cystitis, BPH, chronic prostatitis, or other inflammatory conditions e.g., chronic inflammation associated with joint pain synovitis, or arthritis, as well as, inflammatory bowel disease, Crohn's disease or ulcerative colitis. The aforementioned compositions can also be provided or administered to subjects e.g., orally, rectally, vaginally, parenterally, or topically, to improve skin appearance, skin hydration, skin elasticity, or to accelerate or facilitate wound healing. The extracts used in these compositions can be made from any part of the plant e.g., stems, arils, roots, leaves, inflorescences, or seeds or its roots or root ball and such extracts can be formulated with or without a pharmaceutically, nutraceutically or cosmeceutically acceptable carriers, diluents, preservatives, or excipients. Preferably, one or more preservatives (e.g., Phenoxyethanol, Optiphen™ (Phenoxyethanol and Caprylyl Glycol), Methylparaben or Chlorphenesin) or antioxidants (e.g., a tocopherol or tocotrienol) or both are included in formulations comprising an extract of *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladiumfor* or any combination thereof. It has been found that certain preservatives and/or antioxidants improve the stability and efficacy of such extracts better than others.

In more embodiments, compositions comprising, consisting essentially of or consisting of an extract (e.g., a propanediol extract or extracts made using a liquid C1-C8 alkane solvent, an alcohol, or a mixed solvent containing an alcohol and a C1-C8 alkane or water) of *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladiumfor* or any combination thereof, preferably compositions comprising two or more of such aforementioned extracts are formulated with sunscreens or post-sun care products e.g., creams, foams, gels, or sprays with or without preservatives (e.g., Phenoxyethanol, Optiphen™ (Phenoxyethanol and Caprylyl Glycol), Methylparaben or Chlorphenesin) or antioxidants (e.g., a tocopherol or tocotrienol), or both to preserve, enhance, adjuvant, or improve the free-radical absorbing protection afforded by HA. Similarly, said compositions can be used to ameliorate or inhibit radiation damage in a subject such as a human or non-human animal e.g., rectal or vaginal areas resulting from radiation therapy or solar radiation damage to exposed skin e.g., by applying a topical formulation of said compositions to such tissue regions, such as by a suppository, cream, lotion, spray or foam, prior to, during or after receiving radiation from the sun or radiation therapy or any combination thereof. The disclosed compositions may also be included in cosmetic formulations that are used to restore skin moisture or improve skin appearance in a subject e.g., reducing the appearance of fine lines or wrinkles, scars, dermatitis, psoriasis, or skin allergies. Preferred alternatives include:

1. A composition comprising at least one plant extract (e.g., a propanediol extract or an extract made using a liquid C1-C8 alkane solvent, an alcohol, or a mixed solvent containing an alcohol and a C1-C8 alkane or water) of *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladium*, preferably two or more of said extracts from different plants; and, optionally a pharmaceutically, nutraceutically or cosmeceutically acceptable carrier, diluent, preservative, anti-oxidant, or excipient.

2. The composition of alternative 1, comprising two or more of said extracts from *Illicium verum* (Star Anise), *Tilia* sp. (Linden), or *Prunella vulgaris* (Prunella).

3. The composition of alternative 2, comprising an extract from Star Anise and Linden.

4. The composition of alternative 2, comprising an extract from Star Anise and Prunella.

5. The composition of alternative 2, comprising an extract from Linden and Prunella.

6. The composition of alternative 2, wherein said composition comprises an extract of Star Anise, Linden, and Prunella.

7. The composition of alternative 1, wherein said composition comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of an extract of Star Anise or an amount of an extract of Star Anise that is within a range defined by any two of the aforementioned percentages.

8. The composition of alternative 1, wherein said composition comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of an extract of Linden or an amount of an extract of Linden that is within a range defined by any two of the aforementioned percentages.

9. The composition of alternative 1, wherein said composition comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of an extract of Prunella or an amount of an extract of Prunella that is within a range defined by any two of the aforementioned percentages.

10. The composition of alternative 3, wherein said composition comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of an extract of Star Anise or Linden or an amount of an extract of Star Anise or Linden that is within a range defined by any two of the aforementioned percentages.

11. The composition of alternative 4, wherein said composition comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of an extract of Star Anise or Prunella or an amount of an extract of Star Anise or Prunella that is within a range defined by any two of the aforementioned percentages.

12. The composition of alternative 5, wherein said composition comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of an extract of Linden or Prunella or an amount of an extract of Linden or Prunella that is within a range defined by any two of the aforementioned percentages.

13. The composition of alternative 6, wherein said composition comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, or 97% of an extract of Star Anise, Linden or Prunella or an amount of an extract of Star Anise, Linden or Prunella that is within a range defined by any two of the aforementioned percentages.

14. The composition of alternative 6, wherein said composition comprises an equal amount of an extract of Star Anise, an extract of Linden and an extract of Prunella.

15. The composition of alternative 6, wherein said composition comprises an amount of a mixed extract of Star Anise, Linden and Prunella, wherein said mixed extract in said composition is present in said composition in at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or within a range defined by any two of the aforementioned percentages.

16. The composition of alternative 14, wherein said composition comprises about a third of or a third of an extract of Star Anise, about a third of or a third of an extract of Linden and about a third of or a third of an extract of Prunella.

17. The composition of any one of alternatives 1-16, further comprising an extract from *Pimenta dioica* (Allspice).

18. The composition of any one of alternatives 1-17, wherein the total extract concentration in said composition, preferably a mixed extract comprising an extract of Star Anise, an extract of Linden, and an extract of Prunella, is between about 50 or 50 µg/mL and about 500 or 500 µg/mL, such as 50, 75, 100, 125, 150, 175, 200, 225, 250, 275, 300, 325, 350, 375, 400, 425, 450, 475 or 500 µg/mL or within a range defined by any two of the aforementioned amounts.
19. The composition of any one of alternatives 1-18, wherein said extract is made using an alcohol, or a mixed solvent containing an alcohol, such as alcohol and water, preferably 50% alcohol and 50% water.
20. The composition of any one of alternatives 1-19, wherein said extract is made from stems, arils, roots, leaves, inflorescences, seeds, roots, or root ball of said plants.
21. The composition of any one of alternatives 1-20, wherein said composition comprises a preservative.
22. The composition of alternative 21, wherein said preservative is Benzyl Alcohol, Dehydroacetic acid, Glyceryl Caprilate, Potassium sorbate, Caprylhydroxamic Acid (and) Caprylyl Glycol (and) Glycerin (Spectrastat-Inolex), Geogard® ECT (Benzyl Alcohol & Salicylic Acid & Glycerin & Sorbic Acid), Gluconolactone & Sodium Benzoate, Anisic acid, Glyceryl Caprylate (and) Glyceryl Undecylenate, Ethyl Lauroyl Arginate, Triclosan, Methylisothiazolinone, Methylchloroisothiazolinone, Chlorphenesin, Chloroxylenol, Iodopropynyl butylcarbamate, Methyldibromo glutaronitrile, Phenoxyethanol, 2-butoxyethanol, 2-(2-butoxyethoxy)-ethanol, 2-(2-ethoxy)-ethanol, Quaternium-15, Sodium hydroxymethyl glycinate, Methylparaben, Ethylparaben, Propylparaben, Butylparaben, Isobutylparaben, Benzoic Acid, Sorbic Acid, or Salicylic Acid or any combination thereof.
23. The composition of alternative 21, wherein said preservative is Phenoxyethanol, Optiphen™ (Phenoxyethanol and Caprylyl Glycol), Methylparaben or Chlorphenesin or any combination thereof.
24. The composition of any one of alternatives 1-23, wherein said composition comprises an antioxidant.
25. The composition of alternative 24, wherein said antioxidant is a tocopherol, a tocotrienol, Butylated hydroxytoluene, Butylated hydroxyanisole, Ascorbic Acid, a polyphenol, or a flavonoid.
26. The composition of any one of alternatives 1-25, wherein said composition is formulated in a cream, gel, lotion, spray, ointment, tablets, suppository, lozenge, capsule, powder, granule or solution.
27. A method of inhibiting degradation of hyaluronic acid (HA), such as mediated by HYAL1, and/or reducing the generation of pro-inflammatory HA fragments (e.g., DAMPS) and/or the loss of HMW-HA in a subject in need thereof such as a human or non-human animal, for instance domestic animals (e.g., a dogs or cats) or farm animals (e.g., horse, pig, cattle, sheep, or goats) comprising administering an effective amount of a composition according to any one of alternatives 1-26 to said subject, optionally selecting said subject to receive a medicament, which inhibits degradation of HA, such as selecting said subject to receive such a medicament by diagnostic or clinical evaluation or both.
28. A method of reducing histamine or tryptase release or both in a subject in need thereof, such as a human or non-human animal, for instance domestic animals (e.g., a dogs or cats) or farm animals (e.g., horse, pig, cattle, sheep, or goats) comprising administering an effective amount of a composition according to any one of alternatives 1-26 to said subject, optionally selecting said subject to receive a medicament, which reduces histamine or tryptase release or both, such as selecting said subject to receive such a medicament by diagnostic or clinical evaluation or both.
29. A method of increasing HA presence or persistence in chondrocytes or synoviocytes or both in a subject in need thereof, such as a human or non-human animal, for instance domestic animals (e.g., a dogs or cats) or farm animals (e.g., horse, pig, cattle, sheep, or goats) comprising administering an effective amount of a composition according to any one of alternatives 1-26 to said subject, optionally selecting said subject to receive a medicament, which increases HA or presence or persistence in chondrocytes or synoviocytes or both, such as selecting said subject to receive such a medicament by diagnostic or clinical evaluation or both.
30. A method of improving wound healing or decreasing the amount of time for closure of a wound or both in a subject in need thereof, such as a human or non-human animal, for instance domestic animals (e.g., a dogs or cats) or farm animals (e.g., horse, pig, cattle, sheep, or goats) comprising administering an effective amount of a composition according to any one of alternatives 1-26 to said subject, optionally selecting said subject to receive a medicament, which improves wound healing or decreases the amount of time for closure of a wound or both, such as selecting said subject to receive such a medicament by diagnostic or clinical evaluation or both.
31. A method of treating, inhibiting, or ameliorating a hyaluronic acid-mediated disease, ailment or condition, such as skin aging, osteoarthritis, rosacea, inflammation, e.g., inflammation or itching from insect bites, bladder interstitial cystitis, BPH, chronic prostatitis, or other inflammatory conditions e.g., chronic inflammation associated with joint pain, synovitis, or arthritis, as well as, inflammatory bowel disease, Crohn's disease or ulcerative colitis in a subject in need thereof, such as a human or non-human animal, for instance domestic animals (e.g., a dogs or cats) or farm animals (e.g., horse, pig, cattle, sheep, or goats) comprising administering an effective amount of a composition according to any one of alternatives 1-26 to a subject in need thereof, optionally selecting said subject to receive a medicament, which treats, inhibits, or ameliorates said hyaluronic acid-mediated disease, ailment, or condition or said inflammatory condition, such as selecting said subject to receive such a medicament by diagnostic or clinical evaluation or both.
32. A method of improving skin appearance, skin hydration, skin elasticity, skin protection from radiation damage e.g., from the sun or due to radiation therapy or to accelerate or facilitate wound healing in a subject in need thereof, such as a human or non-human animal, for instance domestic animals (e.g., a dogs or cats) or farm animals (e.g., horse, pig, cattle, sheep, or goats) comprising administering an effective amount of a composition according to any one of alternatives 1-26 to said subject, optionally selecting said subject to receive a medicament, which improves skin appearance, skin hydration, skin elasticity, skin protection from radiation damage or to accelerate or facilitate wound healing.
33. The method of alternative 31, wherein the condition comprises osteoarthritis, synovitis, inflammatory bowel diseases, rosacea, or one or more insect bites.
34. The method of alternative 32, wherein the method improves protection from radiation damage.
35. The method of alternative 33, wherein the condition comprises mosquito or chigger bites.

36. A method of reducing joint pain in a subject in need thereof such as a human or non-human animal, for instance domestic animals (e.g., a dogs or cats) or farm animals (e.g., horse, pig, cattle, sheep, or goats), comprising administering a composition comprising a therapeutically effective amount of a composition according to any one of alternatives 1-26 to said subject, optionally selecting said subject to receive a medicament, which reduces joint pain.

37. The method of any one of alternatives 27-36, wherein the composition is formulated for topical administration.

38. The method of any one of alternatives 27-36, wherein the composition is formulated for oral administration.

39. The method of any one of alternatives 27-38, wherein the subject is a human.

40. The composition of any one of alternatives 1-26 for use as or in a medicament.

41. The composition of any one of alternatives 1-26 for the preparation of a medicament for the treatment, amelioration, or inhibition of skin aging, osteoarthritis, rosacea, inflammation, e.g., inflammation or itching from insect bites, bladder interstitial cystitis, BPH, chronic prostatitis, or other inflammatory conditions e.g., chronic inflammation associated with joint pain, synovitis, or arthritis.

42. The composition of any one of alternatives 1-26 for the preparation of a medicament or cosmetic for improving skin appearance, skin hydration, skin elasticity, skin protection from radiation damage e.g., from the sun or due to radiation therapy or to accelerate or facilitate wound healing.

43. The composition of any one of alternatives 1-26, wherein said composition is provided in an animal feed or liquid, such as an animal kibble, chew, treat, or liquid formula.

44. The composition of alternative 43, wherein said composition lacks an organ food source such as liver, heart, pancreas, or spleen or an extract thereof.

45. A method of making the composition of alternative 43 or 44, wherein said composition is incorporated into said animal feed or liquid such as by spraying on an animal feed, incorporation in said animal feed during processing of the animal feed or formula, vacuum application of said composition into or onto said animal feed or liquid.

46. A food or liquid comprising the composition of any one of alternatives 1-26, preferably lacking an organ food source such as liver, heart, pancreas, or spleen or an extract thereof such as a food or liquid consumable by a human or non-human animal for instance domestic animals (e.g., a dogs or cats) or farm animals (e.g., horse, pig, cattle, sheep, or goats).

BRIEF DESCRIPTION OF THE DRAWINGS

The accompanying drawings, which are incorporated herein and constitute part of this specification, illustrate non-limiting and non-exhaustive embodiments of the present disclosure, and, together with the description provided herein, serve to explain various features of the disclosed technology.

FIG. 3A represents a photomicrograph of wound closure in the experimental system. FIG. 3B is a graph showing the rate of closure measured at various time points.

FIG. 4A shows histamine release and FIG. 4B shows Tryptase release.

DETAILED DESCRIPTION OF THE PREFERRED EMBODIMENT

Figure 1A:
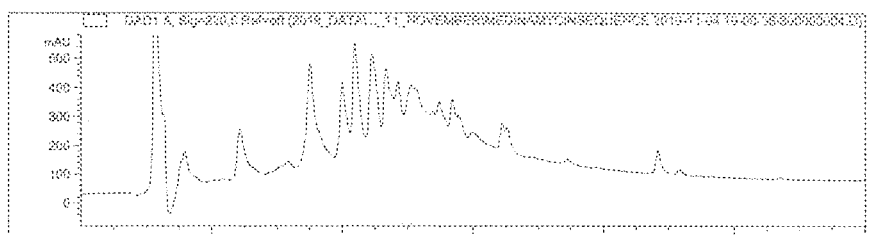
FIGS. 1A-1D show UV chromatograms corresponding to Example 3. The UV chromatogram for *Prunella vulgaris* is provided in FIG. 1A; the UV chromatogram for *Illicium verum* (Star Anise) is provided in FIG. 1B; the UV chromatogram for *Tilia* sp. flowers (Linden) is provided in FIG. 1C; and the UV chromatogram for the combined three-extract mixture is provided in FIG. 1D.

The present disclosure describes compositions comprising plant extracts that effectively inhibit HA degradation by HYAL1, thereby inhibiting the loss of HMW-HA and the resultant production of DAMPS. The disclosed compositions are useful for the effective treatment, inhibition, or amelioration of HA-mediated conditions, such as osteoarthritis, bladder interstitial cystitis, BPH, chronic prostatitis, skin aging and skin appearance including poor hydration and elasticity of skin, wound healing, rosacea, inflammation from insect bites. Other inflammatory conditions, such as periodontitis, dermatitis and inflammatory bowel diseases, such as Crohn's disease or ulcerative colitis may also be effectively treated by the disclosed compositions.

Extracts have been made from plants, actinomycetes and fungi, using the appropriate parts of the organism, for example, flowers, leaves, berries, bark and roots from plants; cultured cells and spent growth media from fungi and actinomycetes. Extracts of each biological material were made in appropriate solvents, generally including a polar solvent, a non-polar solvent and a solvent of medium polarity for each sample being tested. Following extraction, the solvents were evaporated and the dry residues were dissolved in Dimethyl Sulfoxide (DMSO) and assayed for HYAL1-inhibitory activity. Plant extracts, identified by screening assays as having potent HYAL1-inhibitory activity included extracts of: *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladium* and combinations thereof. These particular plant and fungal extracts were identified from more than 2,000 natural product extracts as having especially strong anti-hyaluronidase activity compared to published reports of Hyaluronidase inhibitors, as reviewed in Girish, K. S. et al. Current Medicinal Chemistry 16, 2262-88, 2009.

Extraction solvents useful for the compositions described herein are organic solvents. Examples of suitable organic solvents include, but are not limited to, ethanol, propanediol, dimethyl isosorbide, pentylene glycol, acetonitrile, methanol, isopropanol, 1-butanol, 2-butanol, dichloromethane, ethyl acetate, isopropyl acetate, acetone, butane, hexane, or heptane, or any mixture thereof. In one embodiment, the selected plant component is extracted using 50% ethanol: water as the extraction solvent. In another embodiment, the selected plant component is extracted using propanediol, dichloromethane, hexane, or a mixture thereof.

Other methods suitable for preparing extracts of plant species disclosed herein are described in CA 2,686,931; U.S. Pat. Nos. 5,932,623; 5,882,664; WO 15/55889; WO 11/18763 and EP 2,863,324, the portions of which that identify such extraction methods are hereby expressly incorporated by reference.

The compositions disclosed herein may be pharmaceutical, cosmeceutical or nutraceutical in nature, and are preferably prepared by combining two or more of the disclosed plant extracts with an appropriate pharmaceutically, cosmeceutically or nutraceutically acceptable carrier, diluent, preservative (e.g., Phenoxyethanol, Optiphen™ (Phenoxyethanol and Caprylyl Glycol), Methylparaben or Chlorphenesin) or antioxidants (e.g., a tocopherol or tocotrienol) or excipient. Some compositions also comprise maltodextrin, which is a partially hydrolyzed vegetable starch made from corn, rice, potato starch, wheat, or other vegetable sources. The compositions may be formulated into a variety of preparations, including but not limited to, creams, gels, ointments, tablets, capsules, sprays, suppositories, powders, granules or solutions. Additionally, the compositions described herein can be provided in an animal feed or liquid, such as an animal kibble, chew, treat, or liquid formula. Preferred animal feeds or liquids lack an organ food source such as liver, heart, pancreas, or spleen or an extract thereof. Methods of making such animal feeds or liquids include spraying any one or more of the compositions described herein on an animal feed, incorporation of any one or more of the compositions described herein in said animal feed during processing of the animal feed or formula, or vacuum application of any one or more of the compositions described herein into or onto said animal feed or liquid. Typical routes of administering such pharmaceutical, cosmeceutical or nutraceutical compositions to a subject in need thereof include but are not limited to oral, topical, parenteral, transdermal or sublingual. Cosmeceutical, pharmaceutical or nutraceutical compositions of this disclosure are formulated so as to allow the active ingredients contained therein to be bioavailable upon administration of the composition to a subject. Actual methods of preparing suitable dosage forms are known, or will be apparent, to those skilled in this art. See, e.g., REMINGTON: THE SCIENCE AND PRACTICE OF PHARMACY, 20$^{th}$ Edition (Philadelphia College of Pharmacy and Science, 2000).

The compositions may contain one or more pharmaceutically, cosmeceutically or nutraceutically acceptable carrier, diluent, preservative, (e.g., Phenoxyethanol, Optiphen™ (Phenoxyethanol and Caprylyl Glycol), Methylparaben or Chlorphenesin) or antioxidants (e.g., a tocopherol or tocotrienol) or excipient, which includes but is not limited to any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved by the USFDA as acceptable for use in humans or domestic animals.

Preservatives useful in one or more of the compositions described herein, which comprise an extract (e.g., a propanediol extract or extracts made using a liquid C1-C8 alkane solvent, an alcohol, or a mixed solvent containing an alcohol and a C1-C8 alkane or water) of *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladium* for or any combination thereof, preferably compositions comprising two or more of such aforementioned extracts include any one or more of the following: Benzyl Alcohol, Dehydroacetic acid, Glyceryl Caprilate, Potassium sorbate, Caprylhydroxamic Acid (and) Caprylyl Glycol (and) Glycerin (Spectrastat-Inolex), Geogard® ECT (Benzyl Alcohol & Salicylic Acid & Glycerin & Sorbic Acid), Gluconolactone & Sodium Benzoate, Anisic acid, Glyceryl Caprylate (and) Glyceryl Undecylenate, Ethyl Lauroyl Arginate, Triclosan, Methylisothiazolinone, Methylchloroisothiazolinone, Chlorphenesin, Chloroxylenol, Iodopropynyl butylcarbamate, Methyldibromo glutaronitrile, Phenoxyethanol, 2-butoxyethanol, 2-(2-butoxyethoxy)-ethanol, 2-(2-ethoxy)-ethanol, Quaternium-15, Sodium hydroxymethyl glycinate, Methylparaben, Ethylparaben, Propylparaben, Butylparaben, Isobutylparaben, Benzoic Acid, Sorbic Acid, or Salicylic Acid.

Antioxidants useful in one or more of the compositions described herein, which comprise an extract (e.g., a propanediol extract or extracts made using a liquid C1-C8 alkane solvent, an alcohol, or a mixed solvent containing an alcohol and a C1-C8 alkane or water) of *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladium* for or any combination thereof, preferably compositions comprising two or more of such aforementioned extracts include any one or more of the following: tocopherol, tocotrienol, Butylated hydroxytoluene, Butylated hydroxyanisole, Ascorbic Acid, polyphenols, or flavonoids.

A "pharmaceutical composition," "cosmeceutical composition" or "nutraceutical composition" refers to a formulation of a plant extract of this disclosure and a medium generally accepted in the art for the delivery of the biologically active compound to mammals, such as humans or non-food animals, such as cats, dogs or horses. For example, a pharmaceutical composition of the present disclosure may be formulated or used as a stand-alone composition, or as a component in a prescription drug, an over-the-counter (OTC) medicine, a botanical drug, an herbal medicine, a homeopathic agent, functional food, or any other form of health care product reviewed and approved by a government agency. Exemplary nutraceutical compositions of the present disclosure may be formulated or used as a stand-alone composition, or as a nutritional or bioactive component in food, a novel food, a functional food, a beverage, a bar, a food flavor, a food additive, a medical food, a dietary supplement, or an herbal product. A medium generally accepted in the art includes all pharmaceutically or nutraceutically acceptable carriers, diluents or excipients therefor.

Compositions may contain up to 99 wt % of a particular plant extract, preferably a combination of plant extracts, wherein an equal amount of each plant extract is used. Some compositions may contain, for example, between at least 0.05 wt %-99 wt % of an extract (e.g., a propanediol extract or extracts made using a liquid C1-C8 alkane solvent or water) from *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladium*. That is, some of the aforementioned extracts contain at least 0.05, 0.1, 0.5, 1, 5, 10, 15, 20, 30, 40, 50, 60, 70, 80, 90, or 99 wt % of a plant extract (e.g., a propanediol extract or extracts made using a liquid C1-C8 alkane solvent, an alcohol, or a mixed solvent containing an alcohol and a C1-C8 alkane or water) from *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladium* or any combination thereof or an amount of extract within a range defined by any two of the aforementioned amounts.

In some embodiments, the extracts are present in the composition in equal amounts. In some embodiments a quantity of one plant extract may be used that is greater than the quantities of the other extracts in the composition. That is, in some embodiments an amount of a first extract selected from *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladium*, is mixed with an amount of a second extract selected from *Illicium verum, Tilia cordata, Prunella vulgaris, Pimenta dioica, Spachea correa, Laurophyllus capensis, Sparmania africana Thamnochortus insignis, Smellophyllum capense, Prionium serratum, Horsfeldia amygdalina, Vismia guainensis*, or members of the fungal genus *Tricladium* and the combined amount of first and second extracts is at least 0.05, 0.1, 0.5, 1, 5, 10, 15, 20, 30, 40, 50, 60, 70, 80, 90, or 99 wt % of the composition or an amount within a range defined by any two of the aforementioned amounts. Preferably, said compositions having at least two of the aforementioned extracts have the first and the second extract in equal amounts. In some embodiments, however, the amount of the first extract in the composition is greater than the amount of the second extract in the composition by at least 0.05, 0.1, 0.5, 1, 5, 10, 15, 20, 30, 40, 50, 60, 70, 80, 90, or 95 wt %.

In general, the compositions may be administered to subjects such as a human or non-human animal, for instance domestic animals (e.g., a dogs or cats) or farm animals (e.g., horse, pig, cattle, sheep, or goats) for the effective treatment, inhibition, or amelioration of HA-mediated diseases, ailments, and conditions. Accordingly, the compositions described herein can be used to increase skin thickness, increase hydration or promote healing of the epidermis, alleviate skin dryness (e.g., by increasing the moisture content), or alleviate dryness of lips (e.g., by increasing the moisture content) in a subject. The disclosed compositions can also be used to mitigate the damaging effects of UV radiation on skin of a subject. Thus, by adding the disclosed compositions to a sunscreen formulation or a post-sun care product, for example, the amount of high molecular weight HA in skin can be increased, which is significant because HA is the skin's natural free-radical scavenger. The compositions described herein may also be administered to effectively treat, inhibit, or ameliorate osteoarthritis, synovitis, or joint pain or can be used to alleviate the symptoms of bladder interstitial cystitis, as well as, inflammatory bowel disease, Crohn's disease or ulcerative colitis in a subject. The compositions may also be administered to subjects so as to reduce irritation or itchiness associated with insect bites, or to otherwise treat, inhibit, or ameliorate inflammation, by e.g., inhibiting mast cell degranulation and/or histamine release.

Some of the methods described herein require administration of the disclosed compositions in amounts effective to treat HA-mediated diseases, ailments, or inflammatory conditions such as osteoarthritis, bladder interstitial cystitis, BPH, chronic prostatitis, skin aging and skin appearance including poor hydration and elasticity of skin, wound healing, rosacea, inflammation from insect bites, periodontitis, dermatitis, inflammatory bowel disease, Crohn's disease or ulcerative colitis. Effective topical administration is accomplished by direct application of several grams of the topical dosage form one or more times a day. The effective amount of oral and other dosage forms will depend on patient weight and may range from about 1 to about 20 mg/kg per day administered once or in smaller amounts several times over the course of a day. Effective amounts include combinations of quantities of plant extracts, each of which are effective alone, as well as quantities of plant extracts, each of which may not be sufficient individually, but when combined with other quantities of plant extracts form an effective quantity of plant extract.

As used herein, the terms "treating," "treatment," and "treat" can refer to partially or completely alleviating, ameliorating, improving, relieving, delaying onset of, inhibiting progression of, delaying recurrence of, reducing severity of, and/or reducing incidence of one or more symptoms or features of a particular disease, disorder, and/or condition in certain contexts. For example, treating skin appearance and skin aging may include increasing the hydration and elasticity of the skin.

EXAMPLES

The present invention is next described by means of the following examples. The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification and can be made without departing from its spirit and scope. The invention is therefore to be limited only by the terms of the claims, along with the full scope of equivalents to which the claims are entitled.

Non-limiting examples of suitable combinations of the foregoing extracts include: *Illicium verum* (Star Anise), *Tilia* sp. (Linden), and *Prunella vulgaris* (Prunella); Anise and Linden; Anise and Prunella; Linden and Prunella; Anise, Linden, Prunella, and *Pimenta dioica* (Allspice); etc.

In preparing extracts of Star Anise, the seed pods are separated from the rest of the plant and extracted using an extraction solvent, such as aqueous ethanol. In preparing extracts of Linden, the flowers are separated from the rest of the plant and extracted using an extraction solvent, such as aqueous ethanol. In preparing extracts of Prunella, the flower spikes are separated from the rest of the plant and extracted using an extraction solvent, such as aqueous ethanol. In preparing extracts of Allspice, the berries are separated from the rest of the plant and extracted using an extraction solvent.

Example 1—Isolation of HYAL1

Human HYAL1 enzyme was isolated from urine following published protocols (Afify, A. M. et al. Archives of Biochemistry and Biophysics 305, 434-441, 1993). The enzyme activity was calibrated and validated by comparison to commercially available recombinant human HYAL1 (R&D Systems, USA).

Example 2—Screening, and Selection of Plant Extracts

Initial Screening Assays: More than 2,000 plant extracts were screened for ability to inhibit HYAL1. The initial screening was carried out using a turbidometric ELISA assay following published protocols (Queslati, N. et al. Carbohydrate Polymers, 112 102-8, 2014. Extracts were tested at 10, 5, and 1 mg/ml. Extracts that showed >50% HYAL1 inhibitory activity at 1 mg/ml were selected for further study.

Toxicity Assays: All selected plant extracts were screened for toxicity by measuring their effects on cell growth. As both skin and bladder conditions and osteoarthritis are being targeted, the assays examined the toxicity against the following appropriate cell types:

HaCaT cells: Immortalized human keratinocyte cells used as a model for epithelial cell biology and obtained from ATCC.
Human Dermal Fibroblasts: Established cell lines generated from human skin.
Synoviocytes: Established cell lines generated from bovine metacarpo-phalangeal joints.
Chondrocytes: Established cell lines generated from bovine metacarpo-phalangeal joints.

Cells were plated in 96-well plates in the presence of the test compounds and cell growth was measured using a commercial MTT assay (Abcam, Inc.).

Screening for Effects on HA levels in living cells: Cultured living cells produce HA and secrete it into the medium. The cells also break down the HA using hyaluronidase enzymes. Effective inhibitors would be expected to increase the amount of HA in the culture medium by inhibiting its enzymatic breakdown. As HA also forms the coats around individual cells, the amount of cell-associated HA should increase if its breakdown is efficiently inhibited.

HaCaT cells, Dermal Fibroblasts, Synoviocytes and Chondrocytes were cultured in the presence of candidate inhibitors for 48 hours. The medium was collected and the cells were harvested and lysed. Pooled media and cell lysates were assayed for HA levels using a commercial ELISA assay (Corgenix, Inc.).

Selection of Plant Extracts: The above screening protocols resulted in the identification of a small number of plant extracts as select candidates for further development. This was based on criteria of high inhibition activity in the ELISA screening, lack of overt toxicity in the cell assays, and ability to be bio-available to affect HA concentration in living cells. Extracts were routinely analyzed by HPLC for quality control and identification purposes. Individual extracts and mixtures used in experiments were analyzed in this way, using an Agilent Eclipse Plus C18 column (#959961-902), 4.6×100 mm, 3.5 μm particle size. Method: A=Water with 0.1% TFA, B=acetonitrile with 0.1% TFA. Gradient: 10-100% MeCN over 30 min at a flow rate of 1 mL/min. UV chromatograms are read at a wavelength of 220 nm.

Figure 1B:
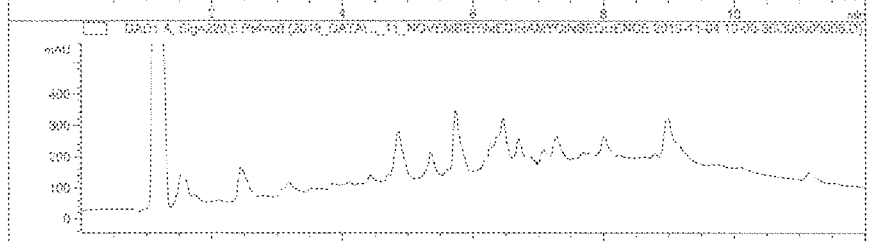
Figure 1C:
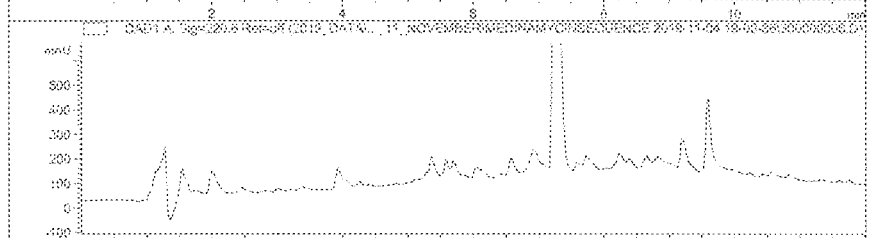
Figure 1D:
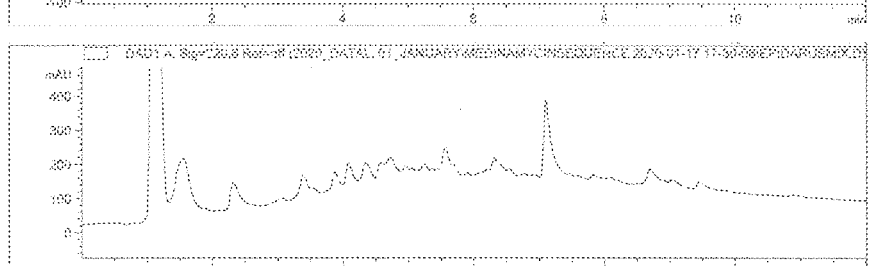

For example, UV chromatogram for *Prunella vulgaris* is provided in FIG. 1A; the UV chromatogram for *Illicium verum* (Star Anise) is provided in FIG. 1B; the UV chromatogram for *Tilia* sp. flowers (Linden) is provided in FIG. 1C; and the UV chromatogram for a combined three-extract mixture is provided in FIG. 1D.

Example 3—Cosmetic Screening Using Skin Models

HYAL1 inhibitors present in one or more of the extracts disclosed herein will increase the amount of HA and moisture when applied to human skin. To demonstrate this beneficial result, testing was conducted on human facial skin that was removed from patients who were undergoing face-lifts. Abdominoplasty and brachioplasty skin was also tested in some experiments. Patients ranged in age from 50 to 65 years and all were female.

The skin was prepared for testing by removing the adipose layer and placing 6 mm punch biopsies on gridded platforms in culture dishes. The test extracts were either added to the culture medium or formulated into a cream and applied to the surface of the biopsies. After 4 days (facial skin) or 8 days (abdominal or brachial skin), the biopsies were fixed in formalin, paraffin-embedded and sectioned for histological evaluations.

HA associated with the treated skin was visualized by staining with Alcian Blue (visualizes polysaccharides in skin—most of which is HA) or by specific HA staining with a Hyaluronic Acid Binding Protein following published protocols.

Figure 2:
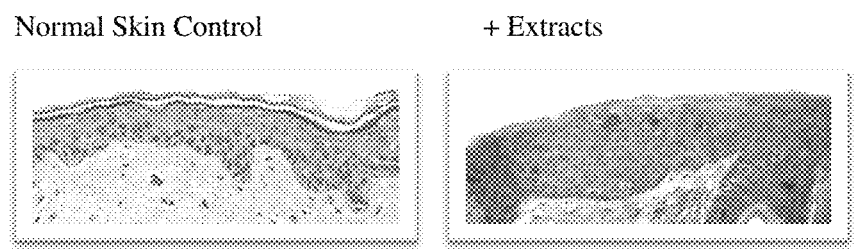
FIG. 2 shows skin sections after topical treatment with candidate extracts.

Plant extracts that caused a visible increase in skin HA in these assays were selected for further evaluation and optimization of topical formulations. Specifically, it was found that skin culture media containing each of Star Anise seed pods extract, Linden flowers extract, Prunella flower spikes extract, and Allspice berries extract caused an accumulation of high molecular weight HA in the epidermis, and a marked increase in the number of epidermal cell layers (epidermal hyperplasia). A typical example of this effect, compared to control skin treated with just the vehicle, is shown in FIG. 2.

Example 4—Wound Healing Assays

Since HA is known to play a major role in skin wound healing, the effects of the selected plant extracts were investigated in cell culture models of wound healing. The standard lab assay for wound healing involves growing cells as a monolayer and creating a wound by scratching the cell layer. The time that it takes for the cells to migrate into the gap and close the wound is measured by microscopy and the data are analyzed using analytical computer software to calculate the rate of healing.

HaCaT cells or Human Dermal fibroblasts were grown in 12-well Tissue Culture plates until the cell layer was confluent. The layer was scratched using a 1 ml pipette tips to make a wound and the rate of wound closure was measured relative to a control. Since wound closure involves two separate processes (cell replication and cell movement), healing measurements were taken in the presence and absence of Mitomycin c, an inhibitor of cell replication, which does not affect cell migration.

All of the selected plant extracts (Star Anise seed pods extract, Linden flowers extract, Prunella flower spikes extract, and Allspice berries extract) exhibited a markedly positive effect on the rate at which epithelial cells migrate into a wounded area and close the gap.

Figure 3:
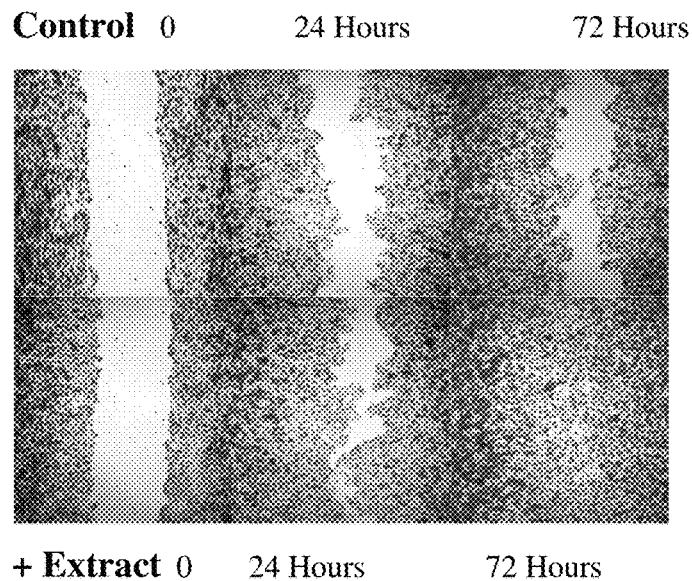
FIGS. 3A and 3B show wound closure over time in the presence of propanediol extracts of Star Anise, Linden or Prunella alone or as a mixed extract of all three, as compared to a vehicle control.
Figure 3:
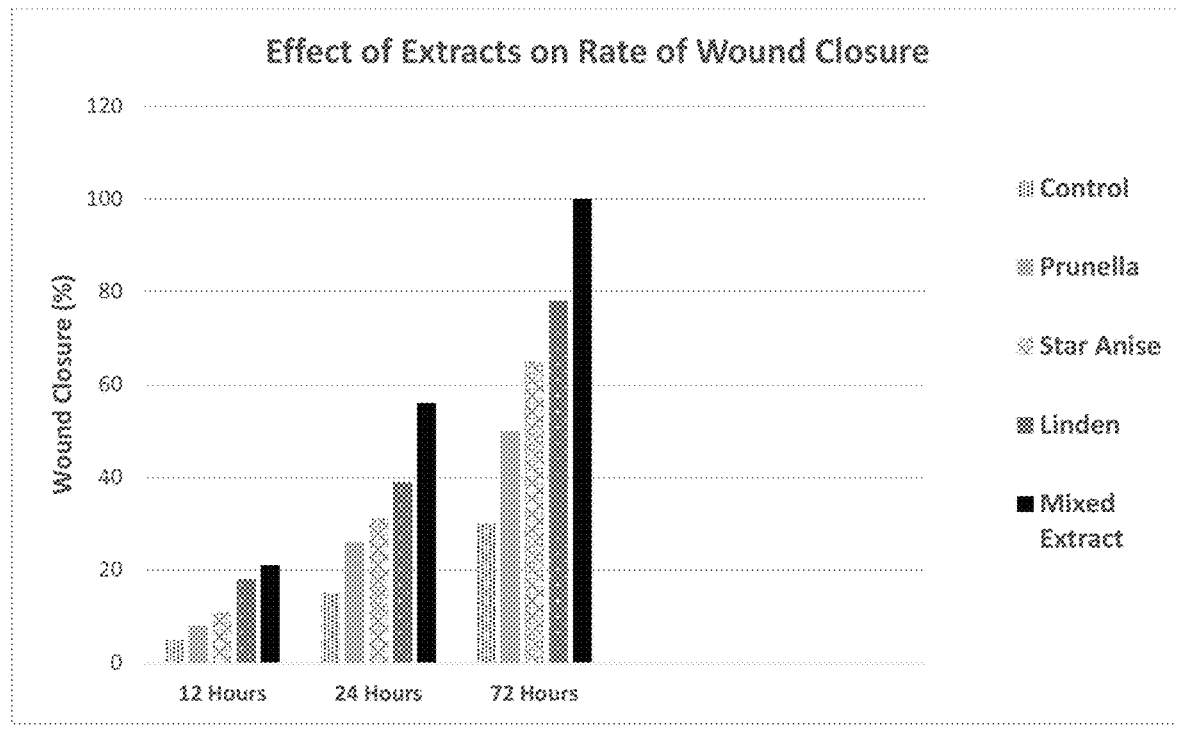

Additionally, vehicle controls were compared to extracts prepared using 50% ethanol/water or 50% 1,3 propanediol/water. It was consistently observed that the selected plant extracts increased the rate of wound closure, and that 1,3 propanediol further enhanced that effect. Data from many experiments were used to arrive at optimal formulation, extraction and delivery protocols. A typical experiment, using a mixed extract, containing equal amounts of Star Anise, Linden and Prunella, in 1,3 propanediol is shown in FIGS. 3A and 3B. FIG. 3A shows a microscopic examination of the wound-healing assays and demonstrates that a mixed extract containing equal amounts of Prunella, Linden and Star Anise causes complete wound closure in 72 hours, while the Control shows only 30% repair of the wound after the same amount of time. FIG. 3B is a graphical representation of the results of several experiments showing wound closure over time in the presence of single extracts or an equivalent concentration of a mixed extract containing all three botanicals.

In addition, Linden and Star Anise were identified as primarily promoters of cell replication, and Prunella as a promoter of cell migration. Since both of these processes combine to effect wound healing, the mixture of these three plant extracts demonstrates a particularly advantageous formulation for use in skin treatments.

Example 5—Mast Cell Degranulation

Figure 4:
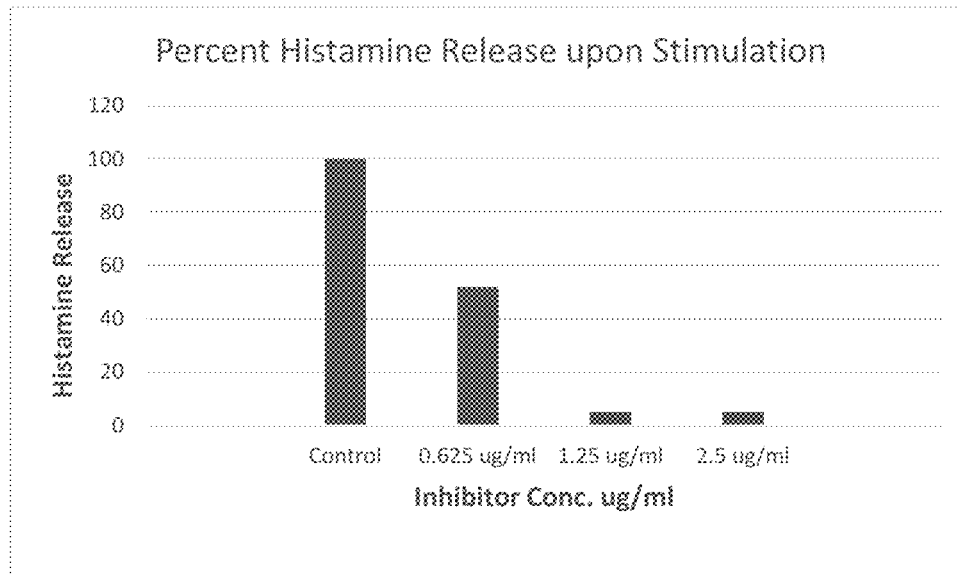
FIGS. 4A and 4B show the effect of extract mix on mast cell degranulation by compound 48/80.
Figure 4:
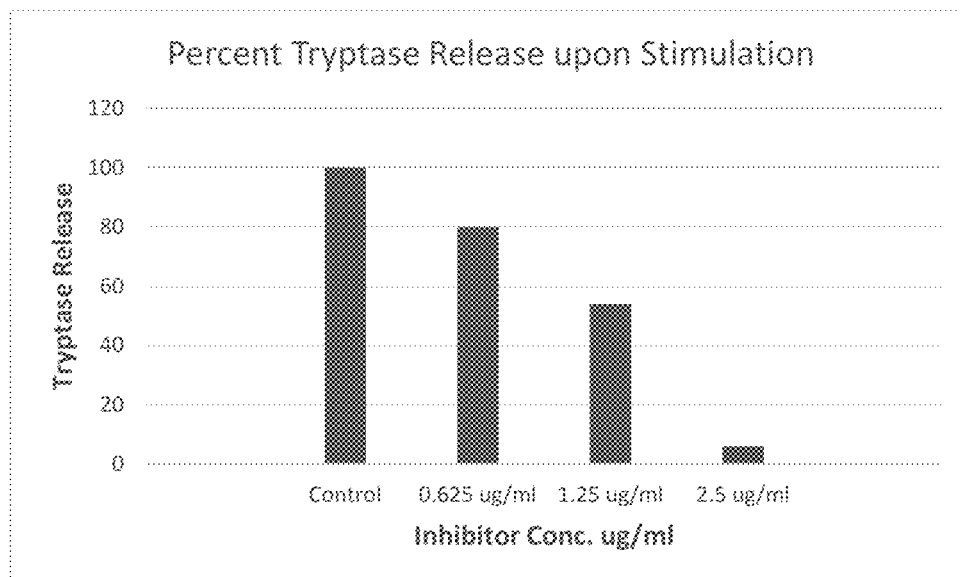

Samples of human facial skin were used as a source of Connective Tissue Mast Cells. The adipose layer was removed from the skin pieces before overnight digestion in Collagenase to release the cells. Mast cells were enriched through culture for 4 weeks as described by Kambe, N. et al. Blood, 97:2045-52 (2001). For degranulation experiments, cells were treated with compound 48/80 (1 ug/ml) for 30 minutes in the presence or absence of an extract mixture containing Star Anise Pod Extract, Linden Flower Extract and Prunella Flower Spike Extract. Inhibition of degranulation was assessed by ELISA assays measuring Histamine release (Cayman Chemicals, Ann Arbor, Mich.) and Tryptase release (Neo Scientific, Cambridge, MA) relative to Control. As shown in FIGS. 4A (Histamine) and 4B (Tryptase), an extract containing Star Anise, Linden and Prunella inhibit degranulation significantly compared to Control.

Example 6—Treatment of Mosquito Bites with Cream Formulation Containing Anise, Linden, and Prunella Extracts This Example describes a study of 20 volunteers with mosquito and chigger bites who were administered a cream formulation comprising a combination of extracts of *Prunella vulgaris* (Prunella), *Illicium verum* (Star Anise), and *Tilia* sp. flowers (Linden). Three different creams were tested (Cream A contained 500 μg/ml Extract Mix, Cream B, 200 μg/ml and Cream C 50 μg/ml) and the effectiveness was ranked by the test participants using a questionnaire.

|   | Very Effective | Somewhat Effective | Not Effective |
|---|---|---|---|
| A | 16 | 2 | 2 |
| B | 15 | 4 | 1 |
| C | 1 | 8 | 11 |

Results show that Creams A and B were ranked as highly effective by the majority of testers, who additionally ranked the Creams as more effective than other, commercially available topical treatments.

Example 7—Effective Inhibition of Hyaluronidase 1 in Cell Models of Osteoarthritis Bovine metacarpopharangeal joints were used as an accepted and representative model for articular joints—e.g., in human knees, hips and shoulders. From the bovine joints, two important cell types were isolated: (i) chondrocytes from the cartilage that covers the bone surface, and (ii) synoviocytes from the synovial membrane. Both cell types are known to produce HA. Synovial fluid was also collected from the joints.

It is believed that the efficacy of pentosan polysulfate in treating osteoarthritis relates to its ability to inhibit HYAL1 (Shen, B. et al. Journal of Pharmaceutical and Biomedical Analysis, 31:83-93, 2003). Accordingly, the efficacy of candidate compositions containing natural plant extracts was compared with that of pentosan polysulfate.

Example 7A: Synovial Fluid

Synovial fluid from healthy joints is a solution of 5 to 7 mg/ml of High Molecular weight Hyaluronic Acid. The bovine metacarpopharangeal joints used in these experiments were from 2 year old steers and the synovial fluid was verified by Agarose Gel electrophoresis to be composed of predominantly High MW HA.

Degradation of Synovial Fluid by urinary HYAL1 breaks down the HA to tetra-saccharides in 2 hours at 37 degrees, using a standard HYAL1 assay, testing 12 ug Synovial Fluid HA per assay. It was determined that pentosan polysulfate caused 100% inhibition of HYAL1 at a concentration of 156 ng/ml in in this assay.

Figure 5:
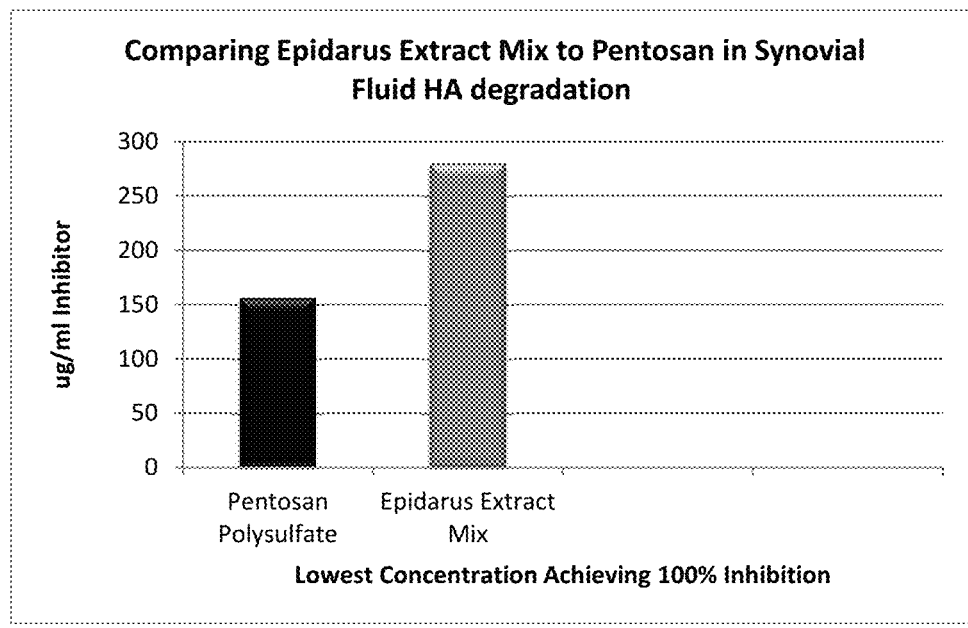
FIG. 5 is a graph showing the concentrations of candidate extracts as compared to pentosane polysulfate, which achieved 100% inhibition of HYAL1 degradation of HA in synovial fluid.

An extract mixture containing Star Anise Pod Extract, Linden Flower Extract and Prunella Flower Spike Extract was also tested to determine the minimum concentration of extract mix required to achieve 100% inhibition of Synovial Fluid HA under the same conditions as used for pentosan polysulfate. This concentration was determined to be 280 ng/ml. The results are shown in FIG. 5.

Example 7B: Chondrocytes and Synoviocytes

Isolated, cultured joint cells were used in an experiment to measure the effects of added HYAL1 inhibitors on HA production by synoviocytes and chondrocytes. Both cell types were isolated from bovine metacarpopharangeal joints. Primary synovial fibroblasts were isolated from the inner layer of the synovial membrane. This tissue was minced and digested with collagenase to release the synoviocytes which were then cultured to expand the cell number and for use in experiments.

Chondrocytes were similarly isolated by collagenase digestion of full depth articular cartilage shavings.

Individual extracts of Star Anise Pods, Linden Flowers and Prunella Flower Spikes were tested, as well as a mixed extract containing all three botanicals. Pentosan polysulfate was included as a positive control. Synoviocytes and chondrocytes were grown in 6-well tissue culture plates and the extracts were added to the culture medium for 24 hours. The medium was harvested and the HA content was assayed by ELISA assays following the manufacturer's protocol (Corgenix, Inc). All extracts, as well as Pentosan were dissolved in DMSO at 10 mg/ml and were tested at a final concentration of 200 ng/ml in the assays.

Figure 6:
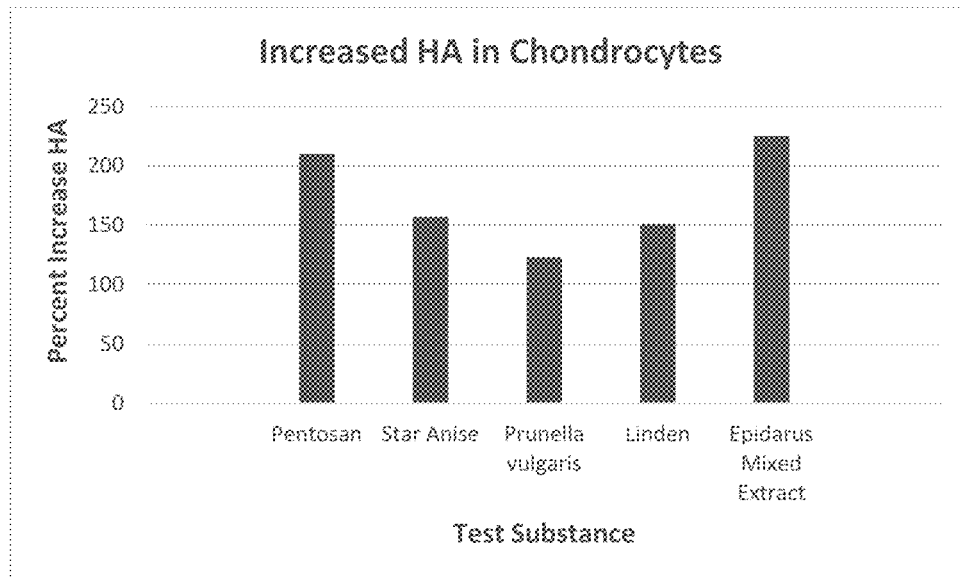
FIG. 6A is a graph showing the percentage increase of HA caused by candidate extracts, as compared to pentosane polysulfate in chondrocytes.
FIG. 6B is a graph showing the percentage increase of HA caused by candidate extracts, as compared to pentosane polysulfate in synoviocytes.
Figure 6:
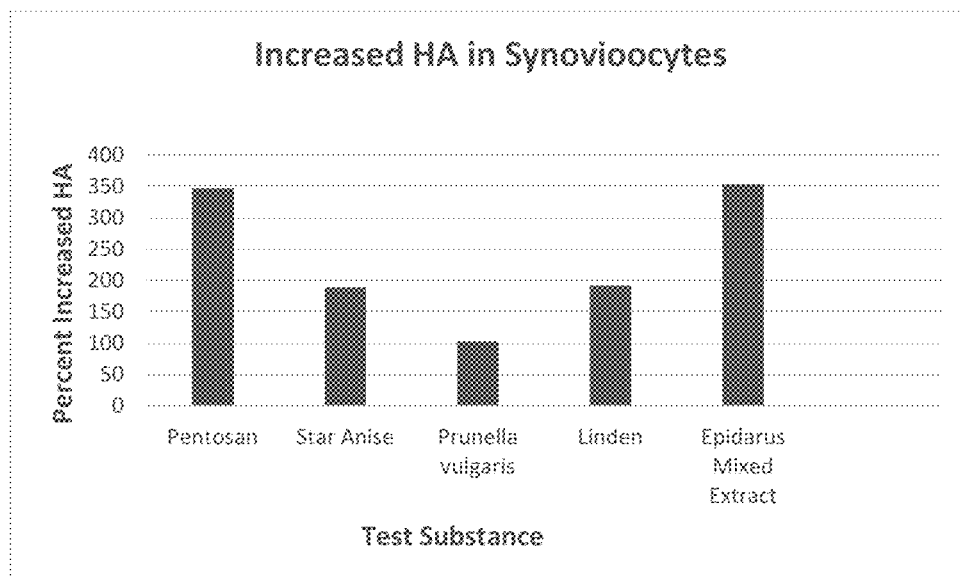

The results are shown in and FIG. 6A (chondrocytes) and FIG. 6B (synoviocytes). It was determined that all the candidate extracts increased the amount of HA in the cell growth medium of both joint cell types. The mixed extract showed a greater effect on HA concentration than any of the individual extracts, exceeding that observed with an equivalent dose of pentosan polysulfate.

Example 7C—Osteoarthritis Model Using Bovine Cartilage Explants

Articular cartilage was harvested from Bovine metacarpophalangeal joints. The cartilage was chopped into ~1 mm³ pieces, and 50 to 60 mg of cartilage was placed in wells of 24-well culture plates.

Figure 7:
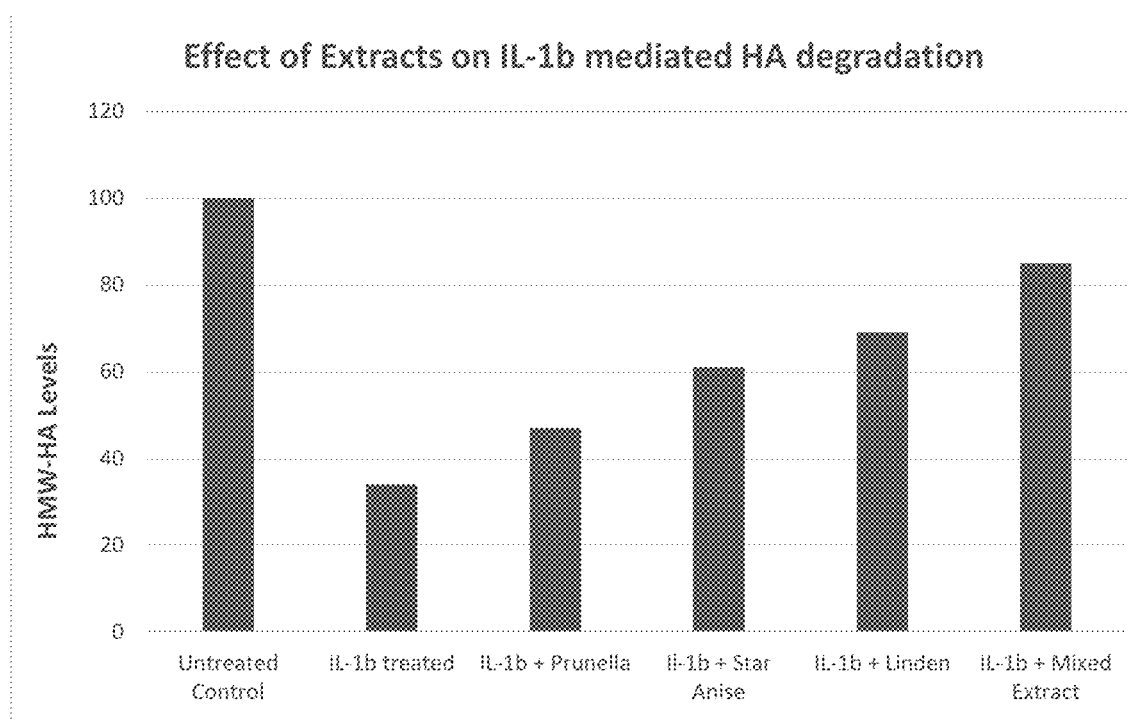
FIG. 7 shows the effect of extracts on IL-1b-mediated degradation of HMW-HA in cartilage explants.

IL-1b was added to model OA inflammation, and the supernatant was collected after 4 days of culture in the presence and absence of candidate extracts. The explants were treated with Pronase to release HA and combined with the culture supernatants for determination of total HA. The concentration of HMW-HA was measured by ELISA. FIG. 7 shows that IL-1b caused a significant reduction in the levels of intact HMW-HA compared to Control, untreated explants. This effect was reversed by the extracts, Prunella, Linden or Star Anise when added alone during explant culture. A equivalent concentration of the mixed extract, containing all three botanicals had an even more pronounced beneficial effect on HMW-HA levels.

These experiments resulted in desirable formulations of extracts for use in clinical testing in osteoarthritis.

Example 8—Cosmeceutical Formulation

In order to achieve stable, bio-active cosmeceutical formulations, a range of commercially available cosmetic ingredients were assessed for their ability to solubilize the Prunella, Linden or Star Anise extracts or mixed extracts of Prunella, Linden or Star Anise without compromising the HYAL1—inhibitory activity of the botanical extracts. These included, for example: Sepigel 305™, Simugel 600™, Arlasolve™-DMI, Carbopol® Ultrez 21, Hydrolyte®5, Hydrolyte®6 and Zemea® 1,3 Propanediol. In addition, a number of preservative/antimicrobial compounds were similarly assessed for efficacy and effects on biological activity of the added botanical extracts. These included, for example: Phenoxyethanol, Optiphen™ (Phenoxyethanol and Caprylyl Glycol), Methylparaben and Chlorphenesin.

The antimicrobial agents were incubated in a solution of 5% 1,3 Propanediol/Water containing 5 mg/ml of Epidarus Extract Mix (Prunella, Star Anise and Linden) at the indicated concentrations for 48 hours at 37 degrees Centigrade. The anti-HYAL1 activity was measured relative to a control without added antimicrobial agents.

Phenoxyethanol at a concentration of 1% was found to preserve anti-HYAL1 activity, while the other antimicrobial agents caused a loss of biological activity.

| Antimicrobial Agent | Anti-HYAL1 Activity |
|---|---|
| Phenoxyethanol (1%) | 100% |
| Optiphen (1%) | 20% |
| Methylparaben (0.3%) | 45% |
| Chlorphenesin (0.3%) | 26% |

The efficacy of 1% Phenoxyethanol was further examined by formulating a range of concentrations of "Epidarus extract mix", comprising Star Anise, Linden and Prunella into creams. The creams were incubated at either 40 degrees Centigrade, 25 degrees Centigrade or frozen at −20 degrees Centigrade. Samples were removed for microbiological testing and for estimation of the anti-HYAL1 potency. Testing was done weekly for 30 days and then at 3 and 6 months and the results of the 6 month test is shown in the table below. These experiments were used to arrive at stable, bio-active cosmeceutical formulations of the Epidarus extracts.

|  | Extract 5 mg/ml (0.5%) | Extract 2 mg/ml (0.2%) | Extract 0.5 mg/ml (0.05%) |
|---|---|---|---|
| Anti-HYAL1 −20 degrees | 100% | 100% | 100% |
| Anti-HYAL1 25 degrees | 100% | 100% | 100% |
| Anti-HYAL1 40 degrees | 100% | 92% | 85% |
| Microbial Count −20 degrees | 0 | 0 | 0 |
| Microbial Count 25 degrees | 0 | 0 | 1 |
| Microbial Count 40 degrees | 0 | 1 | 1 |

Example 9—Nutraceutical Formulation

In order to develop bio-active formulations for osteoarthritis and bladder intertsitial cystitis therapies in humans and animals, oral bio-availability studies were undertaken. To assess bio-availability in canine models of osteoarthritis studies of canine digestion of several formulations of the "Epidarus extracts", comprising Star Anise, Linden and Prunella were used. In a typical example, Epidarus botanical extracts (Star Anise, Linden and Prunella) were dried with maltodextrin (35% Extracts: 65% maltodextrin) to make a free-flowing powder, suitable for use in tablets or in extruded dog chews. Maltodextrin is a partially hydrolyzed vegetable starch and is made from corn, rice, potato starch, wheat, or other vegetable sources.

Gastric digestion was modeled using simulated gastric fluid (SGF-0.2% Sodium Chloride+0.3% Hydrochloric Acid, pH 2.5) in which 1 g of dried Epidarus extract was dissolved in 10 ml of SGF and digested for 2 hours at 37 degrees Centigrade. The gastric digest was adjusted to pH 6.8 with 1M Sodium Hydroxide and mixed with an equivalent volume of Simulated Intestinal Fluid (SIF) to which was added a commercial preparation of canine pancreatic enzymes, at the following concentrations: Lipase (2,000 to 10,000 Units per ml), Protease (100 to 1,000 Units per ml), Amylase (200 to 2,000 Units per ml) and Bile Salts to 10 mM.

Following the simulated complete digestion of the chew/tablet formulations, the levels of active ingredients were assayed and the HYAL1-inhibitory activity was determined. These assays were used to test a range of additives/excipients used in the production of functional nutritional supplements for human and animal use. These include: maltodextrin, dextrose, glucosamine, microcrystalline cellulose, silicon dioxide, stearic acid, sweet potato starch, arabic gum, guar gum, yeast extract, as well as flavorings such as, rosemary oil, white fish extract, liver extract and vegan bacon flavoring.

| Test Ingredient | % Inhibition of anti-HYAL1 activity | Test Ingredient | % Inhibition of anti-HYAL1 activity |
| --- | --- | --- | --- |
| Maltodextrin | 0 | Rosemary Oil | 0 |
| Dextrose | 0 | White Fish Extract | 0 |
| Dicalcium Phosphate | 0 | Nu-Mag Ribus Blend | 0 |
| Microcrystalline cellulose | 0 | Liver Extract Powder | 100 |
| Silicon Dioxide | 0 | Vegan Bacon Flavor | 0 |
| Stearic Acid | 0 | Carrot Powder | 0 |
| Sweet Potato Starch | 100 | Optimizer-Veggie Base | 5 |
| Guar Gum | 20 | | |
| Arabic Gum | 17 | | |
| Yeast Extract | 15 | | |
| Rice extract | 0 | | |

This model system was used to arrive at formulations which preserved the HYAL1-inhibitory activity of the Epidarus extracts and which yielded bio-active products for clinical testing and for product development.

Figure 8:
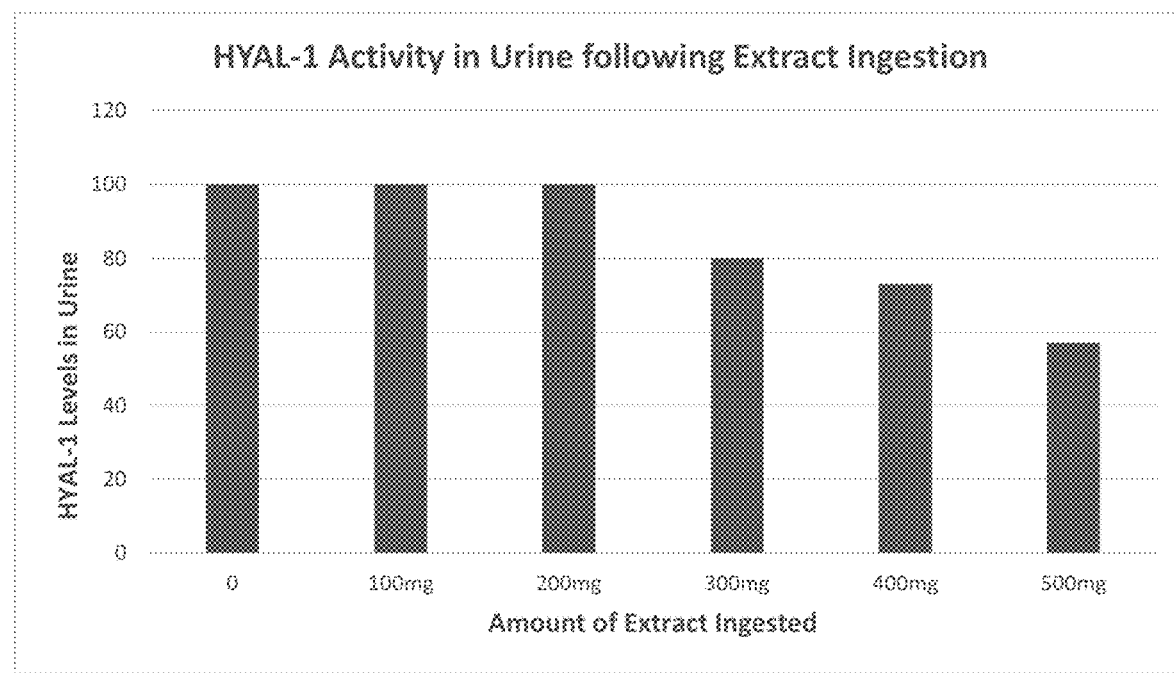
FIG. 8 shows the effect of Star Anise, Linden or Prunella extracts alone or as a mixed extract of all three on HYAL1 activity in urine following oral administration.

Example 10—Effective Inhibition of Bladder Hyaluronidase 1 Following Oral Administration of Extract Mix Containing Prunella, Star Anise and Linden The human bladder is known to produce high concentrations of HYAL1 and to secrete the enzyme into urine, (Csoka, T. B. et al. FEBS Letters 417, 307-310, 1997). In order to examine the oral bioavailability of the anti-HYAL1 activity of the botanical extracts, preparations containing increasing doses of extract were administered. The HYAL1 activity in human urine was measured and compared to the baseline control levels (FIG. 8).

These data indicate that a significant portion of anti-HYAL1 activity can reach the blood stream and, subsequently, the bladder following oral dosing. Inhibitory activity in the bladder underscores evidences the application of the extracts described herein for the treatment, inhibition, or amelioration of bladder interstitial cystitis, BPH and/or chronic prostatitis, since the interplay between the bladder and prostate contribute to LUTS (Lower Urinary Tract Symptoms)

All references cited and/or discussed in this specification are incorporated herein by reference in their entireties and to the same extent as if each reference was individually incorporated by reference.

What is claimed is:

1. A topical composition for treating hyaluronic acid related diseases comprising a therapeutically effective amount of an extract of an *Illicium* species (Star Anise), an extract of a *Tilia* species (Linden), and an extract of a *Prunella* species (Prunella), wherein the composition comprises an equal amount of the extract of Star Anise, the extract of Linden and the extract of Prunella and, wherein the composition further comprises a preservative selected from benzyl alcohol-Benzyl Alcohol, dehydroacetic acid, glyceryl caprilate, potassium sorbate, caprylhydroxamic acid, caprylyl glycol, glycerin, gluconolactone and sodium benzoate, anisic acid, glyceryl caprylate and glyceryl undecylenate, ethyl lauroyl arginate, triclosan, methylisothiazolinone, methylchloroisothiazolinone, chlorphenesin, chloroxylenol, iodopropynyl butylcarbamate, methyldibromo glutaronitrile, phenoxyethanol, 2-butoxyethanol, 2-(2-butoxyethoxy)-ethanol, 2-(2-ethoxy)-ethanol, quaternium-15, sodium hydroxymethyl glycinate, methylparaben, ethylparaben, propylparaben, nutylparaben, isobutylparaben, benzoic acid, sorbic acid, or salicylic acid or any combination thereof.

2. The composition of claim 1, wherein the composition comprises a preservative selected from dehydroacetic acid, caprylyl glycol, glyceryl undecylenate, ethyl lauroyl arginate, triclosan, methylisothiazolinone, methylchloroisothiazolinone, chlorphenesin, chloroxylenol, iodopropynyl butylcarbamate, methyldibromo glutaronitrile, 2-butoxyethanol, 2-(2-butoxyethoxy)-ethanol, 2-(2-ethoxy)-ethanol, quaternium-15, sodium hydroxymethyl glycinate, ethylparaben, or butylparaben.

3. The composition of claim 2, wherein the total mixture concentration of the extract of Star Anise, the extract of Linden, and the extract of Prunella in said composition is between 50 µg/mL and 500 µg/mL.

4. The composition of claim 2, wherein the composition is formulated in a cream, gel, lotion, spray, ointment, tablets, suppository, lozenge, capsule, powder, granule or solution.

5. The composition of claim 1, wherein the composition comprises an extract of *Illicium verum*, an extract of *Tilia cordata*, and an extract *Prunella vulgaris*.

6. The composition of claim 5, wherein the composition comprises a preservative selected from dehydroacetic acid, caprylyl glycol, glyceryl undecylenate, ethyl lauroyl arginate, triclosan, methylisothiazolinone, methylchloroisothiazolinone, chlorphenesin, chloroxylenol, iodopropynyl butylcarbamate, methyldibromo glutaronitrile, 2 butoxyethanol, 2 (2 butoxyethoxy) ethanol, 2 (2 ethoxy) ethanol, quaternium 15, sodium hydroxymethyl glycinate, ethylparaben, or butylparaben.

7. The composition of claim 6, wherein the total mixture concentration of the extract of *Illicium verum*, the extract of *Tilia cordata*, and the extract of *Prunella vulgaris* in said composition is between 50 µg/mL and 500 µg/mL.

8. The composition of claim 6, wherein the composition is formulated in a cream, gel, lotion, spray, ointment, tablets, suppository, lozenge, capsule, powder, granule or solution.

9. The composition of claim 5, wherein the total mixture concentration of the extract of *Illicium verum*, the extract of *Tilia cordata*, and the extract of *Prunella vulgaris* in said composition is between 50 µg/mL and 500 µg/mL.

10. The composition of claim 5, wherein the composition is formulated in a cream, gel, lotion, spray, ointment, tablets, suppository, lozenge, capsule, powder, granule or solution.

11. The composition of claim 1, wherein said composition comprises an amount of a mixed extract of Star Anise, Linden and Prunella that is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% by weight.

12. The composition of claim 11, wherein said mixed extract comprises a third of an extract of Star Anise, a third of an extract of Linden and a third of an extract of Prunella.

13. The composition of claim 1, wherein the total mixture concentration of the extract of Star Anise, the extract of Linden, and the extract of Prunella in said composition is between 50 µg/mL and 500 µg/mL.

14. The composition of claim 1, wherein the composition is formulated in a cream, gel, lotion, spray, ointment, tablets, suppository, lozenge, capsule, powder, granule or solution.

* * * * *

UNITED STATES PATENT AND TRADEMARK OFFICE
CERTIFICATE OF CORRECTION

Page 1 of 3

PATENT NO. : 12,370,231 B2
APPLICATION NO. : 17/905926
DATED : July 29, 2025
INVENTOR(S) : Deirdre O'Sullivan It is certified that error appears in the above-identified patent and that said Letters Patent is hereby corrected as shown below:

In the Specification

Column 4, Line 17, delete "capensis, Sparmania africana" and insert -- capensis, Sparrmannia africana --.

Column 4, Line 19-20, delete "Vismia guainensis, or members of the fungal genus Tricladiumfor or" and insert -- Vismia guianensis, or members of the fungal genus Tricladium for or --.

Column 4, Line 39, delete "capensis, Sparmania africana" and insert -- capensis, Sparrmannia africana --.

Column 4, Line 41-42, delete "Vismia guainensis, or members of the fungal genus Tricladiumfor or" and insert -- Vismia guianensis, or members of the fungal genus Tricladium for or --.

Column 5, Line 59, delete "capensis, Sparmania africana" and insert -- capensis, Sparrmannia africana --.

Column 5, Line 61-62, delete "Vismia guainensis, or members of the fungal genus Tricladiumfor or" and insert -- Vismia guianensis, or members of the fungal genus Tricladium for or --.

Column 6, Line 25, delete "capensis, Sparmania africana" and insert -- capensis, Sparrmannia africana --.

Column 6, Line 27-28, delete "Vismia guainensis, or members of the fungal genus Tricladiumfor or" and insert -- Vismia guianensis, or members of the fungal genus Tricladium for or --.

Column 6, Line 38, delete "capensis, Sparmania africana" and insert -- capensis, Sparrmannia africana --.

Signed and Sealed this
Eighteenth Day of November, 2025

John A. Squires
*Director of the United States Patent and Trademark Office*

Column 6, Line 40-41, delete "Vismia guainensis, or members of the fungal genus Tricladiumfor or" and insert -- Vismia guianensis, or members of the fungal genus Tricladium for or --.

Column 7, Line 3, delete "capensis, Sparmania africana" and insert -- capensis, Sparrmannia africana --.

Column 7, Line 5, delete "Vismia guainensis, or" and insert -- Vismia guianensis, or --.

Column 12, Line 61, delete "capensis, Sparmania africana" and insert -- capensis, Sparrmannia africana --.

Column 12, Line 63, delete "Vismia guainensis, or" and insert -- Vismia guianensis, or --.

Column 14, Line 10, delete "capensis, Sparmania africana" and insert -- capensis, Sparrmannia africana --.

Column 14, Line 12-13, delete "Vismia guainensis, or members of the fungal genus Tricladiumfor or" and insert -- Vismia guianensis, or members of the fungal genus Tricladium for or --.

Column 14, Line 36, delete "capensis, Sparmania africana" and insert -- capensis, Sparrmannia africana --.

Column 14, Line 38-39, delete "Vismia guainensis, or members of the fungal genus Tricladiumfor or" and insert -- Vismia guianensis, or members of the fungal genus Tricladium for or --.

Column 15, Line 6, delete "capensis, Sparmania africana" and insert -- capensis, Sparrmannia africana --.

Column 15, Line 8, delete "Vismia guainensis, or" and insert -- Vismia guianensis, or --.

Column 15, Line 16, delete "capensis, Sparmania africana" and insert -- capensis, Sparrmannia africana --.

Column 15, Line 18, delete "Vismia guainensis, or" and insert -- Vismia guianensis, or --.

Column 15, Line 29, delete "capensis, Sparmania africana" and insert -- capensis, Sparrmannia africana --.

Column 15, Line 31, delete "Vismia guainensis, or" and insert -- Vismia guianensis, or --.

Column 15, Line 35, delete "capensis, Sparmania africana" and insert -- capensis, Sparrmannia africana --.

CERTIFICATE OF CORRECTION (continued)
U.S. Pat. No. 12,370,231 B2

Column 15, Line 37, delete "Vismia guainensis, or" and insert -- Vismia guianensis, or --.

Column 20, Line 9, delete "Bovine metacarpopharangeal joints" and insert -- Bovine metacarpophalangeal joints --.

Column 20, Line 28, delete "bovine metacarpopharangeal joints" and insert -- bovine metacarpophalangeal joints --.

Column 20, Line 51, delete "bovine metacarpopharangeal joints." and insert -- bovine metacarpophalangeal joints. --.

Column 21, Line 42, delete "305TM, Simugel 600TM," and insert -- 305TM, Simulgel 600TM, --.

Column 21, Line 63, delete "Optiphen (1%)" and insert -- OptiphenTM (1%) --.

Column 22, Line 32, delete "bladder intertsitial cystitis" and insert -- bladder interstitial cystitis --.

Column 23, Line 44, delete "Tract Symptoms)" and insert -- Tract Symptoms). --.

In the Claims

Column 23, Claim 1, Line 58, delete "benzyl alcohol-Benzyl Alcohol, dehydroacetic" and insert -- benzyl alcohol, dehydroacetic --.

Column 24, Claim 1, Line 2, delete "propylparaben, nutylparaben, isobutylparaben" and insert -- propylparaben, butylparaben, isobutylparaben --.